United States Patent [19]
Krütten

[11] Patent Number: 4,538,836
[45] Date of Patent: Sep. 3, 1985

[54] UNION FOR MEDICAL INSTRUMENTS OR PIPES AND A FEMALE HALF OF SUCH A UNION

[75] Inventor: Viktor Krütten, St. Wendel, Fed. Rep. of Germany

[73] Assignee: Fresenius AG, Bad Homburg, Fed. Rep. of Germany

[21] Appl. No.: 366,686

[22] Filed: Apr. 8, 1982

[30] Foreign Application Priority Data

Apr. 13, 1981 [DE] Fed. Rep. of Germany ....... 3114937

[51] Int. Cl.$^3$ .............................................. F16L 35/00
[52] U.S. Cl. ...................................... 285/24; 285/331; 285/423; 285/DIG. 22
[58] Field of Search ................. 285/331, 24, 330, 27, 285/332, DIG. 22, 423

[56] References Cited

U.S. PATENT DOCUMENTS

| 3,588,149 | 6/1971 | Demler | 285/331 X |
| 3,768,476 | 10/1973 | Raitto | 285/331 X |
| 3,899,198 | 8/1975 | Maroschak | 285/DIG. 22 |
| 4,133,312 | 1/1979 | Burd | 285/332 X |
| 4,214,586 | 7/1980 | Mericle | 285/DIG. 22 |
| 4,266,815 | 5/1981 | Cross | 285/DIG. 22 |

FOREIGN PATENT DOCUMENTS 2657215 7/1977 Fed. Rep. of Germany.

Primary Examiner—Dave W. Arola
Attorney, Agent, or Firm—Cushman, Darby & Cushman

[57] ABSTRACT

A union or coupling for medical instruments or pipes, more specially for injection, transfusion or infusion has a male half with radial nosepieces for locking it in position and a female half with a guide structure and a keeper part, placed proximally of the guide structure, for fixedly locking the nosepieces on the male half proximally of the locking nosepieces of the female half with the nosepieces on the male half seated in radial pockets in said female half. Each nosepiece on the male half has stop ends running parallel to the axis of the male half and each pocket has opposite stop ends, parallel to the axis of the female part for acting against the stop ends on the spigot nosepieces and stopping turning of the male half in relation to the female half. The locking nosepieces on the female half have proximal stop faces, and each locking nosepiece on the male half may only be moved up against the stop faces on the female half with elastic deformation, and because of the elastic springing back of the structure it is quite impossible for the male half later to be pulled out of the female half, a proximal stop on each nosepiece on the male half being kept in position against the stop face. In this way it is possible to make certain that simply by pushing the two halves of the union into each other without any twisting thereof the locking nosepieces on the male half are guided in guide openings of the front or distal guide structure of the female half to proximally the locking nosepieces thereof and it is then quite impossible for the union to be undone and separated into two halves. If needed the union may be designed so that a sealing function is produced by sealing faces resting fluid-tightly against each other, or the union may be designed as a mechanical fastener only.

9 Claims, 5 Drawing Figures

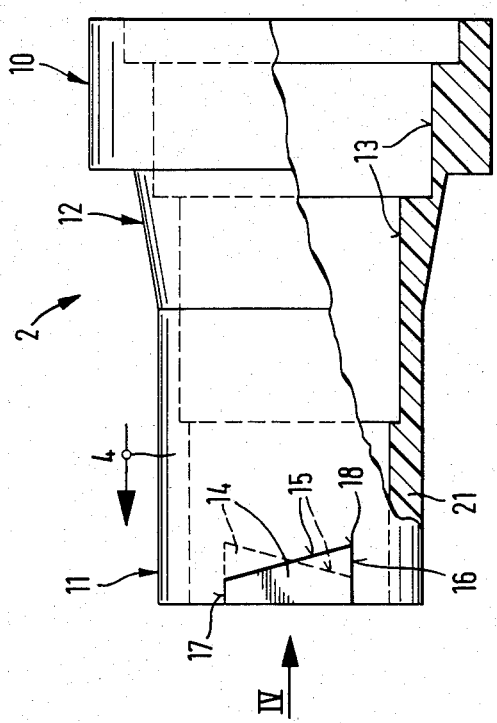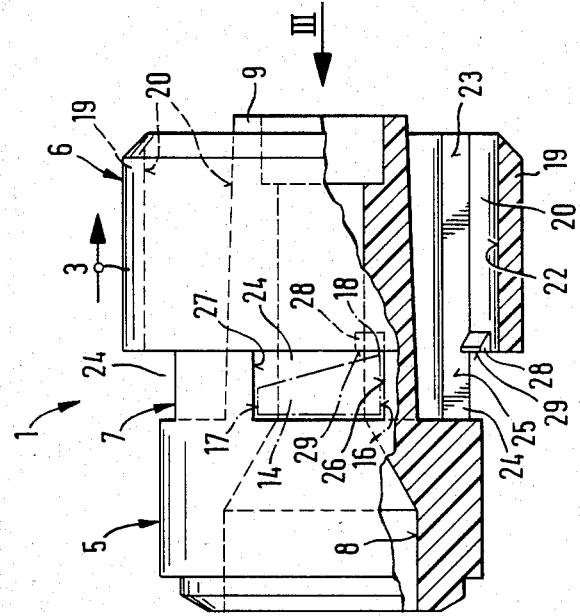

UNION FOR MEDICAL INSTRUMENTS OR PIPES AND A FEMALE HALF OF SUCH A UNION

BACKGROUND OF THE INVENTION

The present invention is with respect to a union for medical instruments or pipes such as catheters, probes and flexible piping generally, more specially for injection, transfusion or infusion. In fact, while the present invention is more specially directed to a union for pipes, it is to be kept in mind that its teachings may generally be used in the design of fastener-like unions without any fluid connection function. The sort of union on which the present invention is more specially based is one having a male half with a solid or hollow spigot of generally round cross-section and having at least one radial nosepiece on its outer face. The union of the invention is furthermore made up of a female part with a middle axis socket for taking up the spigot of the male half, the socket having at least one locking nosepiece in the path of motion of the radial nosepiece on the spigot when the spigot is moved into the socket. Furthermore, the locking nosepiece of the female half is such as only to let the spigot be pushed home into the socket when elastic deformation takes place, that side of the locking nosepiece which is to the back (as seen in the direction of motion of the spigot when moved into position) having a stop face for acting against a back stop, the word "back" again being used in connection with the direction of motion of the spigot into the socket, for acting on such radial nosepiece and locking it into place. The invention is furthermore directed to the female half of the union as such.

The most common make of union or coupling on these lines used in the field is the Luer or Record union, which generally has, on the one half, a union nut, which may be separate or fixed to an instrument, with generally a double-start thread with a helix angle of 12° and within this thread there is a coned pin part with a duct running therethrough. The male half of the union is in the form of a coned spigot with an inner face or bore having the same cone angle, and in the joined-up condition of the union the male half is slipped on the outer coned face of the pin part so as to be rested fluid-tightly against it, that is to say when the male half has its circumferential wall in the space between the thread and the coned pin part. On its outer face the male half has nosepieces, like small lengths or pieces of a screwthread, which are screwed into the two-start female thread of the union nut so that, on turning the female and male halves in relation to each other, such nosepieces will be screwed into the female thread till the pin part is moved right home into the coned spigot or sleeve. However, it is not necessary for all unions to have the mating faces on the pin part and the spigot or sleeve in the form of a cone and in fact only one of the two faces may have a coned form so that there will only be contact along a line between the two parts, such line contact nevertheless giving a full sealing effect. Furthermore, it is possible for the union nut to be joined to a cylindrical stem while the male half is in the form of a cylindrical spigot if the one part is fixed, after being moved right home, in relation to the other by radial stops for example, or if the union is not to be fluid-tight. For doing up the union, the male half with the nosepieces thereon is placed against the female thread of the female half and then the male half is screwed into the female half until, because of the slipping motion of the spigot of the male half in an axial direction in relation to and on the pin of the female half, the union has been done up to the desired degree. In the case of a union with coned sealing faces there will be a high enough degree of static friction between the coned faces forced against each other to keep the parts of the union fixed together. The union nut in addition keeps the two halves fixed together because the nosepieces are screwed into the thread of the union nut. For this reason, the union may not be separated into its two halves when acted upon by a strong pulling or bending force.

More specially in unions in which the male and female halves are made of synthetic resin or plastic, which may be desired for reasons of price because such unions are generally not used more than once, a self-locking effect will be produced in the fully done-up position of the union nut on the thread even although the helix angle of the threads is great, such self-locking effect being caused because of the screwed up threads parts being elastically bent to some degree and, for this reason, locked at such points by static friction; however, this condition may only be produced on using a certain amount of force for doing up the union nut. If, however, the union nut is not done up tightly enough (if the patient makes an attempt at turning the union nut or if the union nut becomes loose and turned out of its fully done-up position for some other reason, the union nut will no longer be locked and tightly done up in position, even in this case of a synthetic resin structure. Such loosening of the union nut may be caused by a small angle of turn, which is unlikely to be seen on examination of the union by eye. However, even in such a condition, in which the union nut has only been unscrewed to a small degree, there will no longer be a positive and full locking effect between the male and female halves, the two only being kept done up by static friction, if in fact the sealing faces are coned or flared. If then the union is acted upon by a pulling or bending force, as will frequently be likely if the union is carelessly handled, the static friction effect will be overcome and in fact it is likely for the male half to come completely out of the female half. The outcome of this will, clearly, be serious and may even be the cause of the death of the patient. If the union nut is made in one piece with the rest of the female half, the female and male parts will have to be turned in relation to each other for doing up the union, the nosepieces on the male half having to be screwed into the female thread of the union nut. These nosepieces are placed at the distal end of the male half (that is to say at its end furthest from the apparatus to which it is joined) so as to make certain that the nosepieces are taken up in the female thread once the male half has only been slipped a small distance into the union nut and overlapped thereby.

One sort of prior art union on these lines is to be seen in German Offenlegungsschrift specification 2,657,215, the union being designed as a quick-release coupling. Its female half has two oppositely placed locking nosepieces at its distal end (that is to say its end furthest from the apparatus with which it is joined), while on the other hand the male half has at its proximal end (the end nearest the apparatus with which it is joined and to the back in the direction in which the male half is moved into the female half doing up the union) a ring-like shoulder around it as a nosepiece or catch. For doing up the union, the front, uncovered spigot of the male half is pushed into the female half so that the spigot is taken up in a coupler of the proximal end of the female half. The male half is slipped in until its proximal nosepiece has been moved past the distal locking nosepieces (with elastic deformation) on the female half and has snapped in or detented in on the proximal side thereof. For making certain that the union may be quickly undone, the distal part of the female half (that is to say the part furthest from the apparatus with which it is joined) may be bent elastically by the user's fingers so that the two diametrally opposite locking nosepieces are moved further away from each other, freeing the ring-like nosepiece on the male half.

Although this prior art union has the useful property of being able to be undone very quickly, this is at the price of its not being completely safe, inasfar as the female half may be bent in error so that the male half will no longer be kept in position. Furthermore, the material of the female half has to be soft in its properties so that it is bent to the desired degree simply by pushing against it with one's fingers. Because of this, the front or distal part of the female half may not be so designed as to give any help in keeping the spigot locked in position. In fact, if pulled upon, the spigot may be pulled clear of the female half and furthermore, if the union is acted upon by a bending force, the proximal locking nosepiece of the female half will be bent because of this so that leaking is likely when the union is acted upon by bending forces and, in fact, the union may be completely separated. In any case, if pulled upon and bent at the same time, the connection will very quickly be broken.

Furthermore, the union of the said German specification 2,657,215 is made with specially matching female and male halves, which may not be used with other makes of unions. In fact, the male half may in no case be used with a screwunion part, as for example part of a Luer-Lok union and if the male half is to be joined up with some other part of the apparatus, it is necessary for all such parts to have female halves of matching design. However, it is frequently the case that a union has to have different properties to be in line with the function of the connection made therewith at any given time; to take an example, a quick-connection-function may be needed which does not have to be very safe while in an other case the connection produced has to be completely safe, that is to say more or less impossible to undo because of some undesired effect. Lastly, many forms of apparatus have connection parts, as for example female halves of standard unions such as Luer unions, and have to be changed in design if they are to be used with a spigot of the union of the said German patent specification 2,657,215; such changes in the design or even the use of a special adapter piece having one end matching the union of German specification 2,657,215 and the other end matching a Luer union, are naturally complex.

SUMMARY OF THE INVENTION

In view of the present stage of development of the prior art, one purpose of the present invention is that of designing a union of the sort noted which may be quite readily designed so that it may not be separated.

A further object or purpose of the invention is that of designing a union male and female halves of which are regularly and truly fixed in relation to each other.

A further purpose of the invention is that of designing a union which is resistant to pulling and bending forces.

A still further purpose of the present invention is that of making a union female half of which may be used with spigots of industry standard screw-unions, more specially Luer unions.

For effecting these purposes and further purposes, the radial nosepiece is placed at the distal end of the spigot of the male half, that is to say at the end thereof furthest from the apparatus with which it is joined, said radial nosepiece stretching around the spigot for an angle of less than 180° and more specially less than 90°, the female half has a guide structure between the locking nosepiece and its distal end, said guiding structure walling in the female opening socket of the female half, and furthermore there is an axial guiding opening for inward motion of the nosepiece on the spigot, for doing up the union, such a guiding opening or channel being on the inner side of the wall of the guide structure. As a further part of the design, the guiding opening has the locking nosepiece of the female half at its proximal end, that is to say the end nearest to the apparatus with which the female half is joined.

It may be seen from this that the nosepiece on the male half is placed at the distal end of the spigot of the male half, unlike the male half of the union of the said German specification 2,657,215. That is to say the nosepiece is placed at a position at which the threaded parts forming keeper nosepieces, are placed in standard Luer unions. On the other hand, in the invention, the female half has a guide structure between the locking nosepiece thereon and its distal end, such guide structure being placed around the spigot of the male half for guiding the same. On selection of a synthetic resin or plastic with the right hardness or rigidity for the male half and the female half such that when acted upon by forces, there is no macroscopic deformation, that is to say deformations able to be seen by the eye, the spigot of the male half is regularly guided and controlled in its motion radially and is safeguarded against bending forces. Taking into account the hardness of the synthetic resin used, the locking nosepiece may readily be so designed that the union produced may be hard to undo by hand, even though this is still possible without needing any tools, if this is needed on a case-to-case basis. More specially, in the last-named case, the locking nosepiece in the female half may have distal ramps thereon up which the spigot nosepiece is run so that the locking nosepiece is bent, if the force is great enough, while the proximal face of the locking nosepiece has a different slope, for example in a radial plane so that, on making an attempt at pushing back the spigot nosepiece, a locking connection or stopping effect is produced and the union may, in fact, not be undone again.

Because the guide structure of the female half is designed for walling in and guiding the outer face of the spigot of the male half at the part on proximal side (with respect to the male half) of the spigot nosepieces, the clearance width of the guide structure has to be less than the radial size of the nosepiece or nosepieces at the distal end of the spigot. In order, nevertheless, to make it possible for the spigot nosepiece or nosepieces, to be moved through the guide structure on doing up the union there is at least one axial opening or channel at the inside of the wall of the guide structure, through which the spigot nosepiece may be moved through the axial part of the guide structure. The circumferential size of the spigot nosepiece makes an angle of markedly less than 180° and, for example, may be limited to an upper value of 160° so that on making the guide channel (designed for taking up the spigot nosepiece) of the right size circumferentially, there will be a great enough support face or land on the inner side of the circumferential wall of the guide structure giving full supporting and guiding function on the outer face of the spigot. However, as a useful further development of the invention, the spigot will have at least two diametrally opposite nosepieces thereon, each having a limited circumferential extent of for example 90° or less, which may be slipped into specially designed guide openings in the female half, and between such openings there will be guide lands for guiding the outer face of the spigot on the male half.

This makes it possible for the female half of the union to be so designed that the stud-like spigot nosepieces may be used with Luer or Record unions and locked in place detentwise so that unions having such industry standard male halves, may be joined up with one or more opposite or matching union halves with union nuts and more specially with the female half of a union of the present invention without any changes having to be made, as for example the use of adapters or the like. On the other hand, a male half as used in a union of the present invention may, without any trouble and quite simply, be so designed that it may be used with a union nut of normal screw-unions like Luer unions or the like, even if it is different in some respects from the standard, specialpurpose male halves of such unions and, to take an example, has a different geometry of the spigot nosepieces. Furthermore, it is naturally possible for female union halves of the present invention to be produced which are not designed, in certain cases, for functioning with industry standard male screw-union parts, if this is not needed in certain cases and, for example, makes it simpler for the union halves to be produced, such a simpler design outweighing limiting the field of use of such parts.

Furthermore, operation of the union of the present invention may take place without any turning of the male and female halves in relation to each other and in fact by making the guide openings longer and stretching past the locking nosepieces, the design may be such that no twisting of the male half in relation to the female half is possible. Furthermore, the union of the present invention takes up little space in a radial direction, because the guide structure of the female half is only a bit larger in diameter than the outer diameter of the spigot nosepiece or nosepieces, the same sticking out only some millimeters radially from the outer face of the spigot part of the male half. Generally speaking, it is, for this reason, possible to say that the circumferential size of the complete union is only larger than the lumen of the duct running through the spigot from end to end by an amount equal to the radial size of the spigot nosepieces and the wall thickness of the guide structure of the female half radially without the guide opening and the wall thickness of the spigot of the male half.

If the male half of the union or coupling of the present invention has an inner duct running therethrough, the design may be made to give further guiding effects and to give a greater resistance to bending loads if the female half has a pin in the axial part of its guide structure which, on doing up the union, is taken up into the distal end of the duct through the male half and the circumferential wall of the spigot of the male half takes up a position between the outer face of the pin and the inner face of the circumferential wall of the guide structure of the female half. The last-named may, in this case, have a duct running therethrough as well and through the spigot, so producing a fluid connection with the duct running through the male half. The outer face of the pin of the female half and the inner face of the duct through the spigot of the male half may be made use of for circumferentially sealing off this fluid connection, in which respect, in the same way as in the Luer Lok or Record union, the circumferential wall of the duct through the male half and/or the circumferential outer face of the pin are coned in order to give a fluid-tight interference fit and seating effect.

Further useful developments of the invention will be seen in the claims.

Further details and teachings, together with their useful effects, of the invention will be seen from the account now to be given of one working example of the invention.

BRIEF DESCRIPTION OF THE DRAWINGS

FIG. 1 is a side view of a female half of a union or coupling of the present invention.

FIG. 2 is a side view of the male half for use therewith.

DETAILED DESCRIPTION OF A PREFERRED EMBODIMENT

Figure 3:
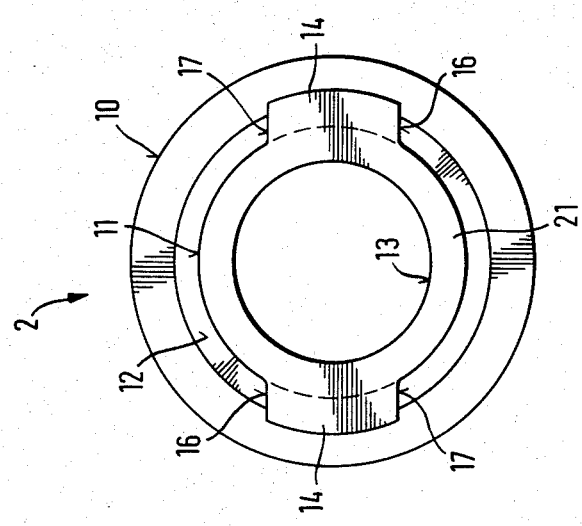
FIG. 3 is an end-on view of the female half of FIG. 1 looking in the direction of arrow III in it.

Turning now to FIGS. 1 and 2, the reader will see on the left hand side a female half 1 and in FIG. 2 a male half 2 for use therewith as a union and able to be put together by being moved in the direction of arrows 3 and 4 axially so that the distal or left hand of male half 2 (the end furthest from the apparatus with which it is fixed) is moved into the distal or right hand end of female half 1. The female half 1, which may be seen on a larger scale in FIG. 5 as a section on the line V—V of FIG. 3, and which may be put on the market as a separate part, has a base part 5, a guide structure 6 and, therebetween, a keeper part 7. A piece of hose, not to be seen in detail in the figure, is so joined up with the base part 5 that the bore within the hose is joined up with a duct 8 running through the base part 5 coaxially. The duct 8 is designed running through the keeper part 7 and the guide structure 6 in a male pin 9 (forming part of the female half 1) running coaxially through the guide structure 6.

The male half 2 as well has a base part 10, a spigot 11 and a part 12 between them joining them together. The male half 2 is generally sleeve-like and has, in the present working example an inner duct 13 running therethrough, which, at any rate, in the spigot 11 has a bore which makes it possible for the pin 9 of the female half 1 to be run into it. The radially outer face of the pin 9 and/or the radially inner wall face of the duct 13 in the spigot 11 may, in a known way, be coned with a cone angle of 1:10 or 1:16.67 for Record unions and, in the second case, for Luer unions to make certain of a fluid-tight pressing fit and seating effect between the two faces. However, the outer face of the pin 9 and the inner wall of the duct 13 may be cylindrical so that the inner wall of the duct 13 may be simply slipped along the outer face of pin 9 without any jamming effect while on the other hand with the smallest possible play. In this case, there is, as well, a radial guiding effect on the spigot 11 of the male half 2 on the outer face of the pin 9, the duct 13 in the male half 2 being outside the spigot 11, that is to say the axial part of the pin 9 might be made solid without any duct, if no fluid connection is desired. In the case of the present example, the union is designed for connections with a fluid and the outer circumferential face of the pin 9 is coned towards the front end of the female half or it may become narrower with a slope or angle of 1:16.67 as is normal for Luer unions. On the other hand, the duct 13 of the male half 2 is cylindrical in the spigot 11, is placed round the front end of the pin 9 with a play therebetween, while the back part gives a fluid-tight interference fit. In place of this, it would furthermore be possible for the circumferential wall of the duct 13 in the spigot 11 of the male half 2 to be coned so as to become wider towards the front or distal end of the male half 2 so as to make generally flat contact against the circumferential face, becoming narrower in the same direction of the pin 9. In the present specification and claims the wording "front" (or distal" end of the female half 1 and of the male half 2, is used for that end, which is nearest the other half of the union so that the arrow 3 with respect to the female half and the arrow 4 used in connection with the male half 2 are each pointing in the "distal" or front direction.

Figure 4:
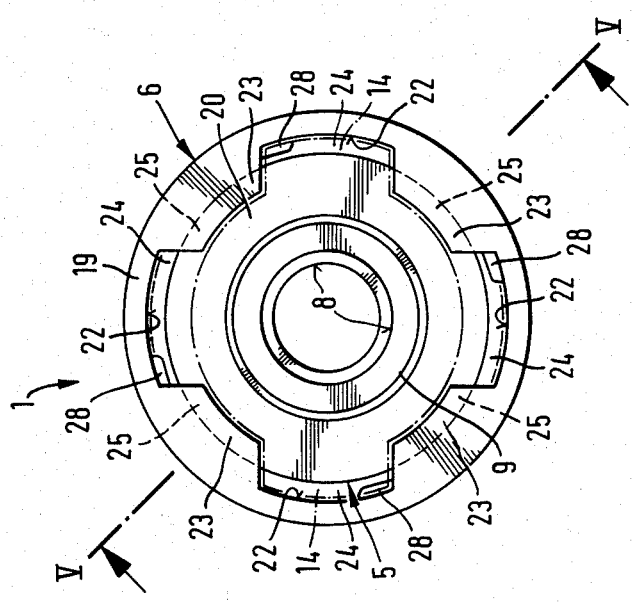
FIG. 4 is an end-on view of the male half of the union of FIG. 2 looking in the direction of arrow IV in it.

At the front or distal end of the spigot 11 of the male half 2 there are, as may be seen in FIG. 4, two nosepieces 14 which are diametrally oppositely placed on the outer face of the spigot 11. Such nosepieces 14 have, in the present example, back faces 15 (see FIG. 2) with a helical angle, that is to say an angle with respect to a transverse plane, of for example 12°, this being in line with the thread helix angle of a normal union nut of a Luer union. This is responsible for the best possible union function when the male half 2 with its spigot 11 is screwed into the union nut of a Luer union. A male half 2 of the sort detailed in the figure is even used for such a Luer union so that, for the male half 2 of a union of the present invention it is possible to make use of, if needed, the male half, presently marketed, for such Luer connections.

In the present example each spigot nosepiece 14 has an angular extent in the circumferential direction which is somewhat less than 90° and side stop ends, facing in the circumferential direction, 16 and 17 and on the back or proximal side, with reference to the direction of arrow 4 of putting in the male half, of nosepiece 14, a stop 18, which in the present example is formed by an edge, which is produced between a side face, forming the stop end 16 and the sloping back face 15 of the nosepiece 14 on the spigot. The function of the stop ends 16 and 17 and of the stop 18 will be made clear later on herein.

Between the thin circumferential wall 19 of the guide structure 6 and the outer face of the pin 9 there is a socket space 20, of ring-like radial cross-section, into which the circumferential wall numbered 21 of the spigot 11 of the male half 2 together with its nosepieces 14 may be slipped until the nosepieces 14 come up against the back side of the guide structure 6 and into the keeper part 7 of the female half 1. As may more specially be seen from FIGS. 3 and 5, the guide structure 6 has four guide openings 22 or channels, equally spaced, that is to say with a center angle therebetween of 90°, there being guide lands 23 between the guide openings, the spigot nosepieces 14 being truly and regularly guided axially in the guide opening 22, as is marked in chained lines in FIG. 3.

The keeper part 7 of the female half 1 has, in line with the guide openings 22, pockets 24, which are placed on the circumferential face of the wall of the keeper part 7 between lands 25, such lands being further parts of guidelands 23. The design of the pockets 24 as radial openings is not necessary in all cases but, however, is simple from the production engineering point of view and makes it readily possible to see by eye if the spigot nosepieces 14 are fully positioned and seated in pockets 24. Pockets 24 have two circumferentially opposite stop ends 26, 27 for use with the stop ends 16 and 17 of the spigot nosepieces 14 so that, when such spigot nosepiece 14 has been pushed home, there is no chance of it being turned in any one of the pockets 24. Because the opposite stop ends 26 and 27 are only at a very small distance from the stop ends 16 and 17 of a spigot nosepiece 14, when pushed home, it is readily possible to see to it that there is no chance of the two union halves being turned in relation to each other. In each guide opening 22 there is a locking nosepiece 28 (which in the present example is near the guide land 23), locking nosepiece 28 running out into the path along which the spigot nosepiece 14 is pushed into the female half. Locking nosepieces 28 may have sloping ramp faces on their proximal or front sides (thought of in connection with the direction of arrow 3) as will be seen in the sectioned part of FIG. 1 so that the radial outer edge of a spigot nosepiece, when pushed home, may be smoothly run up thereagainst and the locking nosepiece 28 may be bent radially outwards with deformation of the circumferential wall 19 (made thin for this purpose) of the guide structure 6. Furthermore, the material of the locking nosepiece 28 may be radially forced outwards as well. Dependent on the material thicknesses used in the design it is then possible, at the same time, for each spigot nosepiece 14 to be bent springingly inwards, the circumferential wall 21 of the spigot 11 of male half 2 being bent to a small degree. Once the spigot nosepiece 14 has been pushed past the locking nosepiece 28 with elastic deformation, there will be a springing back of the one or the other nosepiece, or the two of them, into the radial positions they had at the start, locking nosepiece 28 then offering its back side (thought of in connection with the push-in direction of arrow 3) a stop face 29 which, in the present example, is in a radial plane and is right next to the pocket 24 in the plane of the back face of the guide structure 6. When an attempt is now made at pulling the male half 2 out of the female half 1 against the direction of arrow 4, stop 18 of spigot nosepiece 14 will come up against the stop face 29 (which has springingly moved back into position) of the locking nosepiece 28 so that each spigot nosepiece 14 will be seen to be locked at the back ("back" being used in connection with the pushing-in direction of arrow 3) of the locking nosepiece 28 and, given the right design of stop 18 and of stop face 29, the male half 2 will not be able to be pulled out of the female half 1 in normal use, that is to say it is not separable. If, as in the present example, at least two oppositely placed spigot nosepieces 14 or, if need be, four spigot nosepieces 14 are present, lined up with the guide openings 22 (such spigot nosepieces having the same axial position on the spigot 11 of male half 2), the male half 2 will be symmetrically supported and locked against stops 18 so that the half is regularly and safely locked in position.

Figure 5:
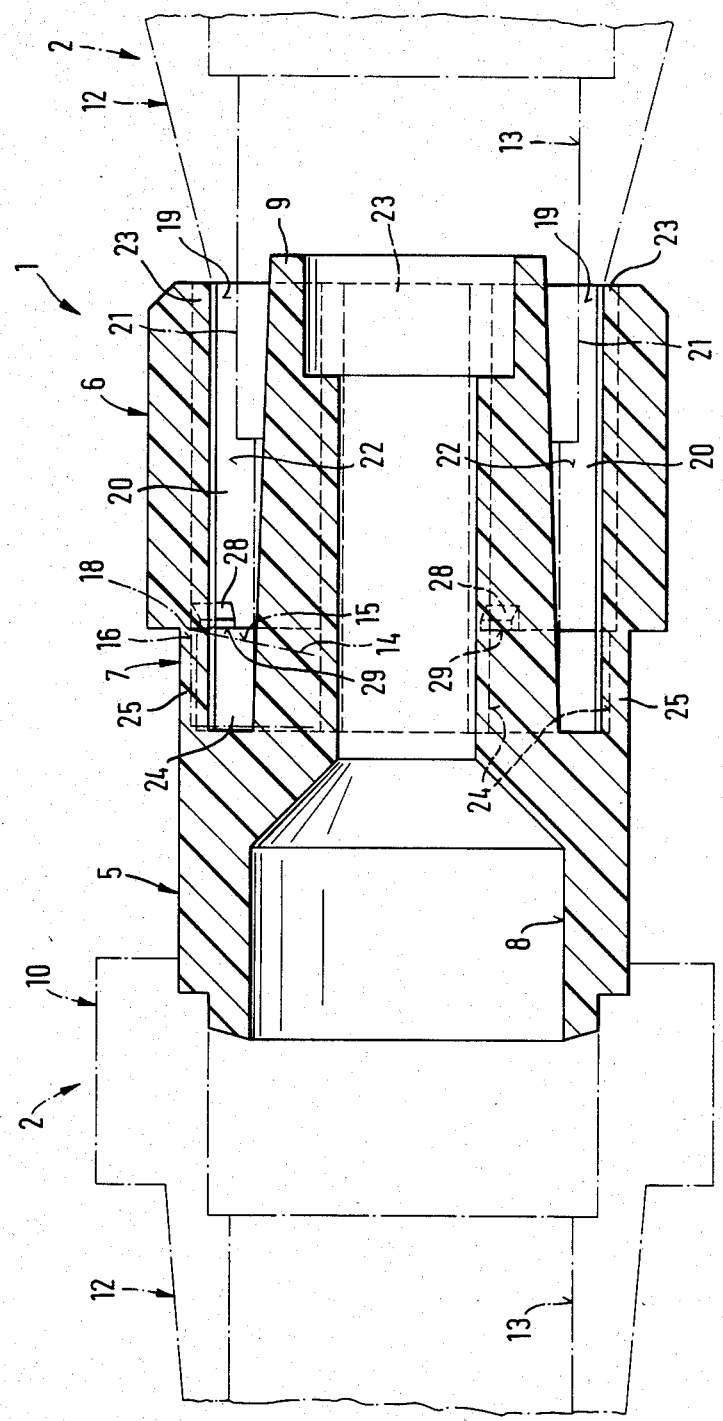
FIG. 5 is a section through the female half as in FIGS. 1 and 3 on the line V—V in FIG. 3, the pushed-home male part being marked in chained lines in its position in relation to the female half.

The base-parts 5 and 10 of the female half 1 and, on the other hand, of the male half 2, are so designed in relation to each other that the base-part 10 of the male half 2 may be placed on base-part 5 of the female half 1 and joined thereto, for example adhesively, as marked in chained lines in FIG. 5, the outcome being a connection unit which, at one end, may be used for taking up a further male half 2, as is marked in chained lines in FIG. 5, while at the other end a female half 1 may be slipped into it. On these lines, ends of pipes may be joined up with end fittings designed like the base-parts 5 and 10 so that they may be fixed on a different form of base-part 10 or 5 or, for example, by adhesive, so that the ends of the pipes may be joined up in the one case with a female half 1 and on the other hand with a male half 2 so that a connection may be made between them using the union of the present invention. It is naturally furthermore possible, however, for base-parts quite different from parts 5 or 10 to be used, such further designs being in line with the form of the parts, not needed for producing the connection of the female half 1 and the male half 2, on a case-to-case basis.

As a general point, the union of the present invention may be used in all cases in which in the field Luer or Record couplings have been used. In this respect, in the way noted, a fluid-tight or non-fluid-tight connection may be produced between the female half 1 and the male half 2 by simply driving home the male part which becomes detented in position. An important point in this respect is that the spigot nosepieces 14, placed at the front or distal end of the spigot 11 of the male half 2 are pushed through the guide structure 6 and locked in position at the back thereof on the locking nosepieces 28, whereas the guide part 6 with the guide lands 23 is placed round the outer circumferential face of the spigot 11 with a small play between the two. Using the right design of the back stop 18 of the spigot nosepieces 14 on the one hand and of the stop face 29 of the locking nosepieces 28 on the other hand, it is possible to make certain of fixing the male half 2 in the female half 1, without any turning thereof, so that there is no chance at all of the two halves being separated and undone, that is to say without damage to the parts. On the other hand, because of the regular and complete guiding of the female half 1 and the male half 2 in relation to each other, the union has a high resistance to strong mechanical forces with, generally speaking, no deformation. If not only the outer circumferential face of the pin 9, but furthermore the inner duct 13 on the spigot 11 of the male half 2 the two are made cylindrical or the two are coned, there will, in this part of the union, be a further supporting of the female half 1 on the male half 2, while on the other hand, if needed, there will be a fluid-tight connection between the ducts 8 and 13 through the union. The male half 2 may, if needed, be joined up with any number of female Luer union parts with union nuts and then pushed into a female part 1 of the present invention so as to be unseparably joined therewith.

It will be noted that in the present specification the union of the invention is made of two halves which typically have not only a male or female function, but furthermore a male or female form. However, this will not necessarily be the case in all possible designs, and in point of fact the two halves may be made without a typically male or female form, as judged purely by eye, such forms of the invention being covered by at least some of the claims:

I claim:

1. A union for medical apparatus, comprising:
a male first half with an axially extending spigot of generally round transverse cross-sectional figure;
said spigot having a front end and a base;
said spigot having at least one nosepiece of limited angular extent circumferentially of the spigot;
said nosepiece being provided on a radially outer face of the spigot so as to project radially outwardly therefrom;
a female second half with an axially extending socket which is constructed and arranged to telescopically coaxially receive said spigot;
said second half having a front end and a base;
said second half having at least one locking nosepiece of limted angular extent circumferentially of said socket;
said locking nosepiece being so located on said second half as to be initially disposed in obstructing relation to completion of telescopic reception of said spigot in said socket;
at least one of said spigot nosepiece and said locking nosepiece being so constructed, arranged and mounted on said second part as to be sufficiently elastically deformably temporarily moved by attempted further insertion of said spigot into said socket after being engaged by said first half, as to permit completion of telescopic reception of said spigot in said socket;
said locking nosepiece having provided on a back side thereof at least one stop face and said spigot nosepiece having provided on a back side thereof at least one stop face, these two stop faces being positioned to engage once telescopic reception of said spigot in said socket has been completed, in such a sense as to cause attempted axial withdrawl of said spigot from said socket while said two stop faces are engaged, to be subject to greater resistance than is said completion of telescopic reception during said further insertion;
said spigot nosepiece being located in the vicinity of the front end of said spigot and extending less than 180° in the circumferential direction of the spigot;
said second half, between said front end thereof and said locking nosepiece, having a guide structure which at least partially encloses said socket;
said guide structure including means providing at least one axially extending, axially frontwardly and radially inwardly opening guide groove for receiving a respective said spigot nosepiece as said spigot is being telescopically received in said socket;
said guide groove having a front and a back located axially opposite one another;
said locking nosepiece being located axially towards the back of said guide groove;
said first half having means defining a duct extending longitudinally therethrough within said spigot;
said second half having an axially extending pin disposed coaxially within said socket;
said pin having a radially outer face which is radially spaced from said guide structure;
said socket being defined at least in part as an annular space of ring-shaped transverse cross-sectional figure radially between said radially outer face of said pin, and said guide structure;
said pin having means defining a duct extending longitudinally therethrough, this duct being constructed and arranged for communication with said duct of said first half upon completion of telescopic reception of said spigot in said socket;

said radially outer face of said pin being conically tapered toward said front end of said second half;

said duct of said spigot being conically flared toward said front end of said spigot, complementarily with said conical tapering of said pin at a cone angle of 1:16.67 for compatability with Luer union parts;

said stop face on said spigot nosepiece being located in an imaginary plane extending at a helix angle of 12° for comparability with a standard Luer union screw nut.

2. The union of claim 1, wherein:

said first half is provided with an even number plurality of said spigot nosepieces, each being located diametrically opposite another;

said guide structure of said second half being provided with a corresponding plurality of said guide grooves; and said second half being provided angularly between said guide grooves with surface means defining lands constructed and arranged for guiding said spigot by engagement with a radially outwardly presented face of said spigot.

3. The union as claimed in claim 2, wherein:

each said spigot nosepiece terminates circumferentially at surface means providing at least one circumferentially acting stop face, said second half having, for each said spigot nosepiece on said first half, surface means providing a pocket which is constructed and arranged to receive the respective said nosepiece in a locked condition of said union, each said pocket having circumferentially acting walls which are constructed and arranged to be acted upon by said stop face of the respective said spigot nosepiece on making any attempt at turning said first half in relation to said second half.

4. The union as claimed in claim 2, wherein:

each said spigot nosepiece is made somewhat undersized in an axial direction in relation to each of said pockets of said second half.

5. The union as claimed in claim 1, wherein:

each said spigot nosepiece is made somewhat undersized in the circumferential direction in relation to each of said pockets of said second half.

6. The union as claimed in claim 1, wherein:

each said locking nosepiece has said stop face thereof formed as part of an edge of a respective said pocket.

7. The union as claimed in claim 1, wherein:

at least one of the pockets is provided in the form of a radially opening aperture.

8. A female second half, for use with a male first half with an axially extending spigot of generally round transverse cross-sectional figure, said spigot having a front end and a base, said spigot having at least one nosepiece of limited angular extent circumferentially of the spigot, said nosepiece being provided on a radially outer face of the spigot so as to project radially outwardly therefrom, said spigot nosepiece having provided on a back side thereof with at least one stop face, said spigot nosepiece being located in the vicinity of the front end of said spigot and extending less than 180° in the circumferential direction of the spigot, said first half having means defining a duct extending longitudinally therethrough within said spigot, said duct of said spigot being conically flared toward said front end of said spigot, and said stop face on said spigot nosepiece being located in an imaginary plane extending at a helix angle of 12° for compatability with a standard Luer union screwnut, said female second half comprising:

means providing an axially extending socket which is constructed and arranged to telescopically coaxially receive said spigot;

said second half having a front end and a base;

said second half having at least one locking nosepiece of limited angular extent circumferentialy of said socket;

said locking nosepiece being so located on said second half as to be initially disposed in obstructing relation to completion of telescopic reception of said spigot in said socket;

said locking nosepiece being so constructed and arranged and mounted on said second part as to be sufficiently elastically deformably temporarily moved by attempted further insertion of said spigot into said socket after being engaged by said first half, as to permit completion of telescopic reception of said spigot in said socket;

said locking nosepiece having provided on a back side thereof at least one stop face, this stop face being positioned to engage said stop face on said spigot nosepiece once telescopic reception of said spigot in said socket has been completed, for resisting axial withdrawal of said spigot from said socket;

said second half, between said front end thereof and said locking nosepiece, having a guide structure which at least partially encloses said socket;

said guide structure including means providing at least one axially extending, axially frontwardly and radially inwardly opening guide groove for receiving a respective said spigot nosepiece as said spigot is being telescopically received in said socket;

said guide groove having a front and a back located axially opposite one another;

said locking nosepiece being located axially towards the back of said guide groove;

said second half having an axially extending pin disposed coaxially within said socket;

said pin having a radially outer face which is radially spaced from said guide structure;

said socket being defined at least in part as an annular space of ring-shaped transverse cross-sectional figure radially between said radially outer face of said pin, and said guide structure;

said pin having means defining a duct extending longitudinally therethrough, this duct being constructed and arranged for communication with said duct of said first half upon completion of telescopic reception of said spigot in said socket;

said radially outer face of said pin being conically tapered toward said front end of said second half complementarily with said conical flaring of said duct of said spigot at a cone angle of 1:16.67 for compatability with Luer union parts.

9. A female union half for establishing a tubing connection for medical apparatus, said union half being integrally made of somewhat elastically deformable synthetic resin material and comprising:

a tubular base part constructed and arranged to be mounted to medical apparatus;

a tubular pin extending coaxially from said tubular base part;

the tubular base part and tubular pin together providing an internal longitudinally duct opening at opposite ends of said union half;

said tubular pin externally conically tapering to the respective end of said union half and providing a radially inner surface for a socket;

a guide structure in the form of a thin annular collar coaxially spacedly surrounding said tubular pin;

said annular collar being connectedly based on said base part so as to provide a radially inner surface for said socket;

means defining at least one radially opening guide groove in said radialy inner surface of said annular collar, said guide groove also opening towards said respective end of said union half;

means defining at least one slot radially opening through said annular collar near said base, said slot intersecting and extending laterally across a respective said guide groove;

said slot defining means including a wall surface bounding said slot, this wall surface being constructed and arranged to act as a stop means against rotation of such male union half spigot lateral protuberance as may telescopically enter said socket on such spigot through said respective end sliding along in said guide groove towards said base part until such lateral protuberance pops into said slot; and means providing at least one radially inwardly projecting protuberance on said radially inner surface of said annular collar bordering an axially forward edge portion of said bounding wall surface of a respective said slot;

said radially inwardly projecting protuberance including a ramp-like forward face and an erect rear stop face, this protuberance being thereby constructed and arranged to facilitate and permit passage of said male union half spigot lateral protuberance therepast as such male union half spigot is telesopically non-rotatively inserted in said socket, but thereafter to resist telescopic non-rotative withdrawal of said spigot from said socket.

* * * * *